United States Patent [19]

Yokoyama

[11] 4,317,458

[45] Mar. 2, 1982

[54] ELECTRODE APPARATUS FOR PACING

[75] Inventor: Masayoshi Yokoyama, Tokyo, Japan

[73] Assignee: Kabushiki Kaisha Top, Tokyo, Japan

[21] Appl. No.: 142,846

[22] Filed: Apr. 22, 1980

[30] Foreign Application Priority Data

Apr. 26, 1979 [JP] Japan .............................. 54/56835[U]

[51] Int. Cl.³ ............................................. A61N 1/04
[52] U.S. Cl. ................................. 128/784; 128/419 P
[58] Field of Search ..................... 128/419 P, 784, 785

[56] References Cited

U.S. PATENT DOCUMENTS 3,416,534 12/1968 Quinn .............................. 128/419 P
3,516,412 6/1970 Ackerman ...................... 128/419 P
3,533,403 10/1970 Woodson ........................ 128/419 P
4,166,469 9/1979 Littleford ........................ 128/419 P Primary Examiner—William E. Kamm
Attorney, Agent, or Firm—Haseltine and Lake

[57] ABSTRACT

An electrode apparatus for cardiac pacing suitable for use in an emergency in which there is provided a needle, a sheath and an electrode needle wire. First, the chest wall is pierced through with the needle covered with the sheath. Thereafter, the needle is pulled out from the sheath and, in place thereof, the electrode needle wire is inserted and subsequently the heart is pierced with the electrode needle wire in preparation for the pacing operation.

1 Claim, 8 Drawing Figures

ELECTRODE APPARATUS FOR PACING

BACKGROUND OF THE INVENTION

This invention relates to an electrode apparatus for cardiac pacing. Such a pacing operation is often carried out for a cardiac patient for regulating the beat of the heart. An electrode connected to a pacemaker is inserted into a human body from the outside for piercing the heart and sending to the heart a very weak electric current periodically. For this operation, it has been usual that the electrode for pacing is inserted so that a long catheter for the electrode may be introduced to the interior of the heart from a vein of the arm or the leg. This process, however, is inconvenient in that it consumes quite a long time because of a technical difficulty, so that it often happens that it cannot meet the needs of an emergency case.

Accordingly, it has been described hitherto to exploit an electrode apparatus for pacing which can serve for an emergency case. The inventor of this application has succeeded in providing an electrode apparatus for pacing which is suitable for use in an emergency case and can achieve a pacing operation. The test results of various trial products are basing on reviewing such a pacing principle that the pacing itself can be obtained simply by interconnecting between a pacemaker installed outside the human body and the heart through a conductive wire.

SUMMARY OF THE INVENTION

An object of this invention is to provide an electrode apparatus for pacing in which the heart can be pierced easily and directly without fail by an electrode wire for giving a stable electric current, by a simple process and for a short time period even in an emergency case.

Thus, according to this invention, there is provided a pacing electrode apparatus which comprises a needle for making a piercing hole in the chest wall of a human body. A plastic made tubular sheath covers the needle with the exception of a short pointed portion of the needle and is slidable and removable in relation to the needle. An elastic electrode needle wire is adapted for piercing the heart through a hollow opening of the sheath after the needle is pulled out subsequently to piercing the chest wall with the needle together with the sheath.

DESCRIPTION OF THE PREFERRED EMBODIMENT

Figure 1:
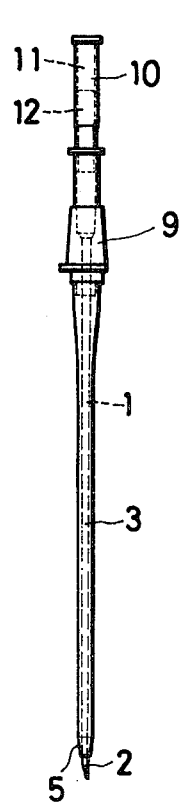
FIG. 1 is a front view of an assembly of a needle and a sheath in one embodiment of this invention apparatus.
Figure 2:
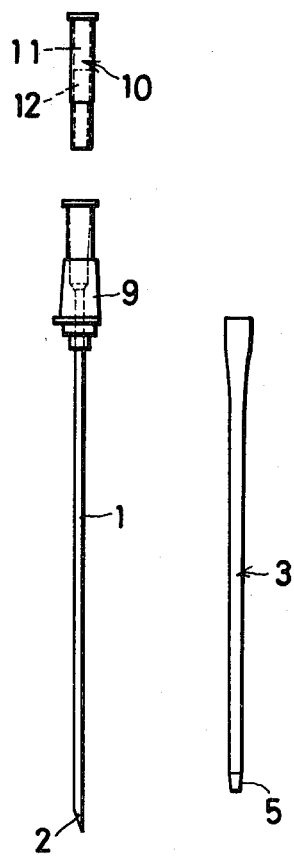
FIG. 2 is a front view of a disassembled condition of the same.
Figure 3:
FIG. 3 is a front view of an electrode needle wire in the same example.

One embodiment of this invention will now be explained with reference to the accompanying drawings:

Referring to FIGS. 1 and 2, reference numeral 1 denotes a needle and numeral 2 denotes a sharp pointed portion of the needle 1. This needle 1 is a cylindrical hollow one like a syringe needle and is 1.5-2.0 mm in its outer diameter a greater part of the needle 1, with the exception of the sharpened pointed portion 2, is covered by a sheath 3. This sheath 3 is a comparatively soft plastic cylindrical bodiy having of 2.0-3.0 mm in its outer diameter, and is so loosely put on the needle 1 as to be able to slide along on it and be pulled off the needle 1 by finger tips. The sheath 3 is formed, at its forward end portion, into a taper 5 so that when the chest wall a is pierced with the needle 1, the sheath 3 can be also passed therethrough. FIG. 3 is a side view of a platinum or stainless steel made electrode needle wire 4 of 0.3-0.5 mm in its outer diameter. A greater part thereof is insulated with an insulation coating 4a of fluourine-contained resin such as "Teflon" or the like which is 0.1-1.2 mm in thickness, and a forward end portion 6 and a rearward end portion 7 thereof are not insulated so as to form an electrode and a connecting terminal which is enlarged in diameter. Numerals 8a, 8b denote criterion marks provided on the insulation coating 11 as guide marks for serving to prevent the electrode needle wire 4 from being inserted too deep, and in this case it is convenient that the length extending from the lower criterion mark 8a to the tip of the needle wire 4 is equal to the length of the sheath 3, and the distance between the two criterion marks 8a, 8b is equal to the length (about 2 cm) of the electrode portion 6. In the illustrated embodiment, the two marks 8a, 8b are indicated by both ends of a colored portion of predetermined length.

Referring to FIG. 1 and 2, numeral 9 denotes a tubular base member attached to the base end portion of the needle 1, and a tubular cup 10 is detachably mounted in the tubular base member 9. The tubular cup 10 is provided in its communicating hollow opening 11 with a water-repellent filter 12 for preventing blood through the needle 1 from spouting outside. Numeral 13 denotes a tube mounted on the rear portion of the electrode needle wire 4 for the purpose of fixing the wire 4 in place.

Figure 4:
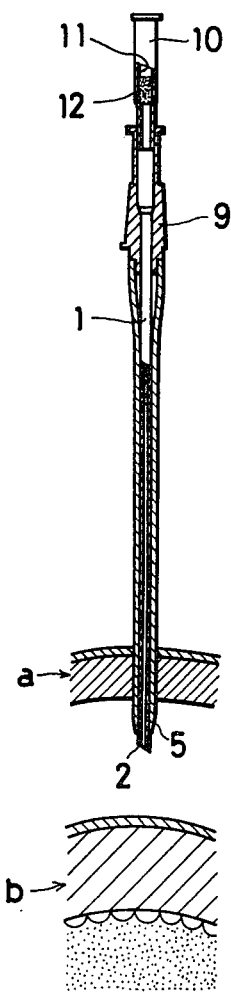
FIGS. 4 to 8 are explanatores diagrams of the manner of use of this invention apparatus.
Figure 5:
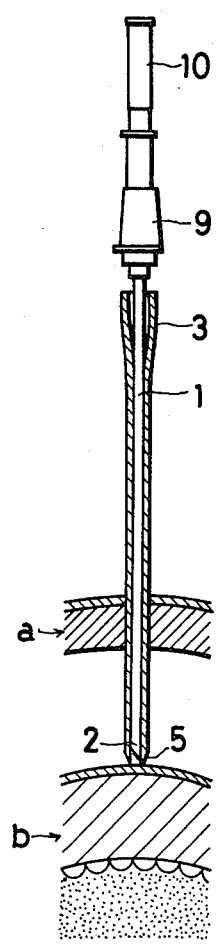
Figure 6:
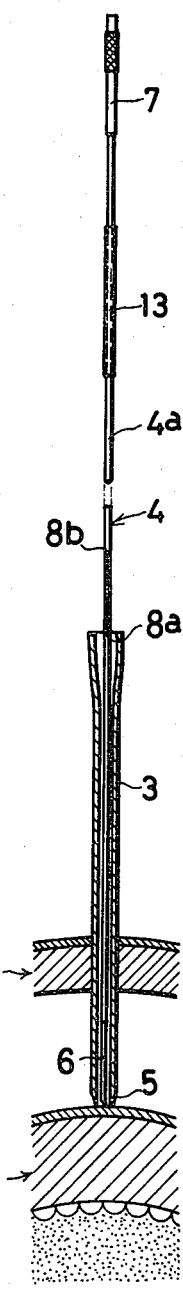
Figure 7:
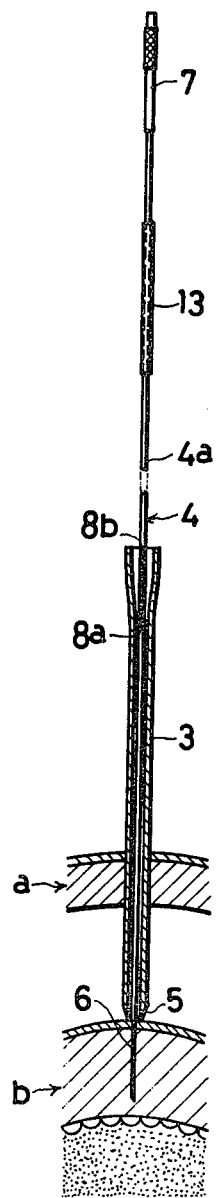
Figure 8:
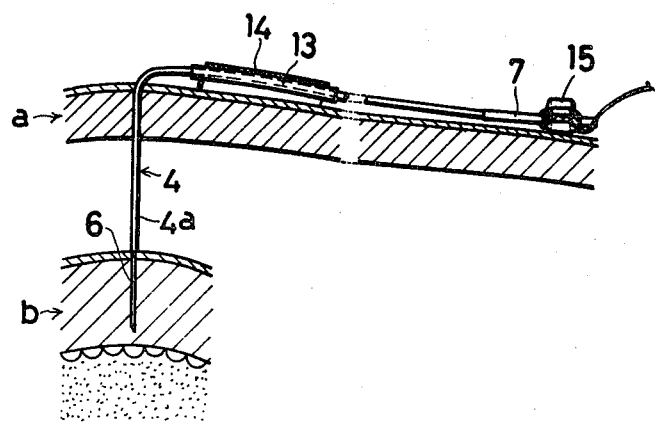

The manner of use of this invention apparatus will be explained with reference to FIGS. 4 to 8 as follows:

First, the skin of the chest wall a is slightly cut, and the needle 1 along with the sheath 3 covering the needle 1 is introduced through that cut portion so to pierce the chest wall a, as shown in FIG. 4. Thereafter, as shown in FIG. 5, the needle 1 is pulled back slightly into the sheath 3 and then in this condition the sheath 3 is advanced until it comes contact with the heart b. Next, the needle 1 is pulled out and the electrode needle wire 4 is inserted into the hollow opening of the sheath 3 to the extent that the lower criterion mark 8a of the wire 4 comes to a level with the rear end of the sheath 3, as shown in FIG. 6. Thereafter, as shown in FIG. 7, the electrode needle wire 4 is further advanced to pierce the heart b to such a deep extent that the upper criterion mark 8b of the wire 4 comes to on a level with the rear end of the sheath 3. Thereafter, as shonw in FIG. 8, the sheath 3 is pulled out, and the electrode needle wire 4 is bent at its middle portion and is fixed through the tube 13 to the skin by means of an adhesion tape 14 extending across the tube 13, and the rearward end portion 7 of the wire 4 is connected by a connecting conductor clip 15 of a pacemaker (not illustrated). In this condition, an electric current is applied from the pacemaker to the wire 4 for effecting the pacing operation.

In the illustrated embodiment, the needle 1 is a hollow one, but may be so modified that the same is a solid one. In the former case, if the needle 1 happens to pierce a blood vessel, blood goes up outside through the needle 1 and thereby such an undesirable piercing can be recognized, and can be changed into a proper piercing for avoiding any further danger.

As for the plastic materials for the sheath 3, fluorine-contained resin which is very low in adhesion property is preferably used, because the sheath 3 is kept in its pierced condition for a time and so tends to adhere to the tissue of the chest wall *a*. Other soft plastic materials such as rubber or synthetic resins, for instance, polypropylene resin, polyethylene resin or the like can be also used.

The insulation coating 4*a* covering the electrode needle wire 4 can be formed by baking of coated material thereon or by mounting an insulation tube on the wire 4. As for the material for this coating 4*a*, fluorine-contained resin is suitble because of its low adhesion property to the tissue of the chest wall *a*.

Thus, according to this invention, the heart *b* can be pierced in the electrode needle wire 4 only by such a manner that the needle 1 along with the sheath 3 is passed through the chest wall *a*, and then the needle 1 is pulled out and the wire 4 is inserted therethrough, so that the pacing operation can be achieved easily and rapidly and the apparatus can be suitably used for in an emergency necessity.

What is claimed is:

1. An apparatus for cardiac pacing comprising: a hollow needle for making a piercing hole in the chest wall of a person; a plastic tubular sheath covering the needle with the exception of a sharp-pointed portion of the needle; said plastic tubular sheath being slidable and removable in relation to said needle; and an elastic electrode needle wire insertable into said sheath adapted for piercing the heart of the person through a hollow opening of said sheath after said needle is pulled out subsequently to piercing the chest wall by said needle together with said sheath; said sheath being formed at its forward end portion into a taper; said electrode needle wire having an insulation coating applied at its greater part, with the exception of a forward end portion and a rearward end portion thereof; said electrode needle wire having upper and lower criterion marks; said lower criterion mark being spaced from the top of said electrode needle wire by a length equal to the length of said sheath, said criterion marks being spaced from each other by a distance equal to the length of a forward end portion of said electrode needle wire.

* * * * *